United States Patent [19]
Villa

[11] Patent Number: 6,132,741
[45] Date of Patent: Oct. 17, 2000

[54] USE OF IMMATURE ALMONDS AS A SKIN BALM

[76] Inventor: Cynthia Marian Villa, 6788 Alicante Ct., Reno, Nev. 89523

[21] Appl. No.: 09/160,923

[22] Filed: Sep. 25, 1998

[51] Int. Cl.$^7$ ....................................................... A61K 7/00
[52] U.S. Cl. ........................................ 424/401; 424/195.1
[58] Field of Search ................................ 424/195.1, 401; 554/10

[56] References Cited

U.S. PATENT DOCUMENTS

| | | | |
|---|---|---|---|
| 4,224,319 | 9/1980 | Marcadet | 424/238 |
| 5,431,911 | 7/1995 | Reynolds | 424/401 |
| 5,492,894 | 2/1996 | Bascom et al. | 514/18 |
| 5,503,832 | 4/1996 | De Stoutz | 424/195.1 |
| 5,643,583 | 7/1997 | Voultoury et al. | 424/401 |

OTHER PUBLICATIONS

The United State Pharmacopeia The National Formulary, (USP 24/NF 19) p. 2412, 1999.
Salunkhe and Desai, Postharvest Biotechnology of Fruits, vol. II, pp. 100–101 (CRC Press, Inc., Boca Raton, Florida, 1986).
Guenther, The Essential Oils, vol. Five, pp. 48–54 (D. Van Nostrand Company, Inc., New York, 1952).
Childers, Modern Fruit Science Orchard and Small Fruit Culture, pp. 382–384 (Horticultural Publications, New Brunswick, New Jersey, 1969).

*Primary Examiner*—Thurman K. Page
*Assistant Examiner*—P. McQueeney
*Attorney, Agent, or Firm*—Charles Hartman; Adrienne Yeung; Skinner, Sutton, Watson & Rounds

[57] ABSTRACT

Skin is moisturized using the extract of the immature almond. The almond is harvested in the immature state and the immature nut is pulverized to produce a liquidy paste that can be applied to the skin of an individual in need of treatment for dry skin.

11 Claims, No Drawings

USE OF IMMATURE ALMONDS AS A SKIN BALM

BACKGROUND OF THE INVENTION

1. Field of the Invention

This invention relates to the production and exploitation of fruits and nuts, particularly this invention relates to the production and exploitation of the drupacious fruits and nuts, and most particularly this invention relates to the production and the exploitation of the almond nut.

2. Background of the Invention

It is not a matter of common knowledge, now well understood in industry and commerce, that the sources of the almond nut is a fruit tree. The sweet almond (known variously by the botanical names of *Prusnus amygdalus, Amygdalus communis*, and *Prunus dulces*) is specifically a stone fruit also known as a drupe, in which the fleshy part, the mesocarp or hull, is derived from the ovary of the flower and surrounds the endocarp or shell, the teguement or thin papery covering of the nut, and finally the stone or nut itself. Almond trees are currently cultivated commercially solely for he value of the edible nut, or in the case of the bitter almond, for the flavoring extracts expressed from the otherwise inedible nut. Almonds are most closely related to other stone fruit, such as peach (*Prunus persica*), apricot (*P. armenisca*) and plum (*P. domestica, P. instititia*, et al.), characterized by having inedible stones, in the common understanding, for seeds of the fruit, and an eminently edible mesocarp (which is not referred to as a hull in the case of peaches, plums and the like). The edible mesocarp forming the basis for the commercial exploitation of peaches, plums and the like, are closely related to the hull of the almond.

Although the closely related fruits are grown throughout the nation, California is the only place in North America where almonds are grown commercially. In the past 30 years, California's almond yield has quadrupled. More than 400,000 acres in the lush San Joaquin and Sacramento valleys are under cultivation, stretching 400 miles between Bakersfield, Calif. and Red Bluff, Calif.

The process of growth, maturation, abscission, and senescense of the almond fruit, is such that early in its growth stage the hull can be eaten by humans processing pleasing taste, texture, and nutritional value, whereas by maturation and thereafter the hull is leathery in texture and astringent to the taste, although its nutritional value has actually increased. Unfortunately, this increase in nutritional values is accompanied by the presence of other chemical components which can temporarily sicken a human. Because most all of the almonds are grown in California, the overall process is well known and can be predictably timed.

Production of a good harvest requires a good chill during November and December which must be followed b a warmer January and February. The leaf-less almond trees then bloom. The almond tree can not pollinate itself; therefore, a productive orchard requires the presence of at least two of the five or so commercial varieties of trees available. Bees pollinate alternating rows of almond varieties. For optimum harvest, the orchards preferably remain frost-free with mild temperatures, preferably averaging between about 55 to 60 degrees Fahrenheit, and receive little rain from February onward so blossoms can flourish and bees can do their job most effectively. Because of the weather requirements, California's central valley provides nearly an ideal climate for the production of almonds.

In later Spring, the flower petals drop and new leaves appear on the trees. Then the first signs of the fuzzy gray-green "fruit" appear. As the fruit continues to mature it hardens and, in July or thereabouts, the outer covering of the fruit or hull begins to split open. Between mid-August and late October, the split slowly widens, exposing the shell of the kernel, allowing the kernel containing the nut to dry. The whole nut and stem finally separate and, shortly before harvest, the hull opens completely.

The farmer then harvests the almonds in the hull and separates and sells the nuts and other by products from the almond. Currently, in addition to the other products on the market, the almond industry now sells the hull. Any products which can be produced, in addition to the nuts and hulls, would aid in the continued commercial success of the almond industry.

Almost hulls form as a part of the almond fruit itself—indeed, as previously noted, in comparing almonds and peaches, for example, the hull is the fruit. They are produced as a by-product of producing the most-utilized part of the almond fruit, namely the stone or nut.

As recently as thirty years ago, the nutritional value of the almond hull was not sufficiently understood to induce almond growers to use them in a rational commercial sence. Consequently, after harvesting nuts, the hulls were either used for landfill, burned for removal, or perhaps burned for their fuel value.

Approximately thirty years ago, agricultural scientist in California introduced and pioneered the use of almond hulls in animal feed, primarily for cattle. Cattle are able to tolerate the chemical components which are unhealthful to humans and the supplemental nutrition of the hulls provides a low cost feed for the farmer and in turn, financially benefit the grower.

In U.S. Pat. No. 4,997,489, Rabinowitz observed that several chemical components of almond hulls, present after fruit maturation, have individual and commercial value, and devised a commercial process to separate and purify each of them, while producing little waste. As an example of the benefit this process and similar processes have for the industry, prior to the introduction of the use of hulls for animal feed, almond hulls had a negative or zero commercial value, but he value quoted therein for feed usage at the date of issuance of the above identified patent for almond hulls was an average of about $50/ton.

Although almonds are widely used as food, and the hulls are now used as cattle feed and sources for other valuble chemicals, other new uses are always needed for the industry to keep developing. One potential use is as a skin medicament. It has now been found that immature almonds seem to have the beneficial skin effects of aloe vera—another plant used for its natural healing powers for the skin.

The aloe vera plant grows in semi-tropical climates and produces a fleshy, succulent, lance-shaped leaf. The leaf has jagged edges set with thorny spines along the outer edges thereof and quires structural rigidity by a plurality of hair-like connective fibers which run throughout the leaf. The plant is the source of at least two medicinal substances. The first is a mucilaginous yellow fluid which comes from the base of the leaves of the plant adjacent to the leaf rind. This yellow fluid is known as aloin and has been used throughout history as an active ingredient in cathartics and medicinal purges. The second medicinal substance produced by aloe vera is the clear gel taken from within the body of the elongated leaves. The gel is used in the preparation of medicinal compositions, cosmetics, soaps, medicants, and the like. Extracting the gel from the leaf poses some problems since the leaf must first be split lengthwise in order to make the gel accessible for recovery.

The therapeutic efficaciousness of the clear gel taken from aloe vera leaves is a function of the freshness of the gel. For other applications, it has been found the relatively old, unstabilized gel has been effective. This difference is apparently a function of the fact that the gel itself is a complex mixture of components which are affected in varying degrees by exposure to air and light at different temperatures and which may vary from batch to batch of gel.

One of the goals of aloe preparation has been to preserve its medicinal efficacy as well as stabilize it for use in cosmetic preparations. Aloe Vera is typically prepared wit heat to pasteurize the formulation. This can cause rapid destabilization of the preparation, so recently cold processes have been developed. Cold processes for preparing aloe vera gel are known which use the whole leaf of the aloe vera plant. However, these processes usually contain a chemical compound that is used for the purpose of killing bacteria.

The search for other natural products that provide some of the benefits of aloe vera continues. It has been discovered that immature almonds can be used as skin medicaments. It is known that varieties of natural products can be beneficial to the skin, acting as moisturizers and protectants of the skin.

SUMMARY OF THE INVENTION

This invention provides a method and balm wherein skin is moisturized using the extract of the immature almond. The almond is harvested in the immature state and the immature nut is pulverized to produce a liquidy paste that can be applied to the skin of an individual in need of treatment for dry skin.

One aspect of this invention is a skin moisturizing agent comprising:

the nut of the immature almond.

Another aspect of this invention is a method for skin moisturization comprising:

obtaining immature almonds;

removing a fruit hull from the immature almond;

extracting a juice of the immature almond; and administering the juice of the immature almond to a portion of the skin that is in need of moisturization.

Yet another aspect of this invention is a method of processing almonds to make a skin moisturizing composition comprising:

obtaining the immature almond;

removing a fruit hull from the immature almond;

pulverizing the immature almond into a juice that is applyable to the skin of a person.

DETAILED DESCRIPTION OF THE PREFERRED EMBODIMENT

An immature almond is defined herein to mean any almond tat has not yet fully hardened into a nut. The immature almonds are harvested in late July or early August before the kernel has hardened and the inner gel-like nut is removed and processed into a soothing skin emolent. The soft nut produces a gel-like product that can be processed to produce a gel, juice, or other liquidy products useful for the preparation of medicinal compositions, cosmetics, soaps, medicants, and the like.

In one embodiment of this invention, various natural products can be extracted and the products can be separated and exploited individually. The success of this process depends upon understanding the physiology and biochemistry of the immature almond fruit and the precise application of commercial separation science techniques to selectively extract components of value without destroying or otherwise causing the loss of any of the components. Using careful extraction techniques with the immature almond nut, organic acids such as critic, malic, and quinic acids can be produced.

In a more preferred embodiment, the immature seeds or nuts are pressed to produce the liquidy gel that is used as a medicament or emolient without further processing.

It has been observed that the therapeutic efficaciousness of the gel taken from the immature almond is a function of the freshness of the gel. For some applications, it has been found that relatively old, unstabilized gel will be effective, but it is greatly preferred that the gel be preserved by such means as freezing. In one preferred embodiment, the immature fruits are stored in a protective covering, such as plastic bags or the like, as wholes in the freezer.

One of the goals of almond preparation will be to preserve its medicinal efficacy as well as stabilize it for use in cosmetic preparations. Both heat and cold preparations using anticeptic chemicals can be used.

In some embodiments of this invention, the entire immature fruit can be pressed to form a liquidy gel of a different composition than the usual composition made from just the nut alone. Again, both hot and cold processes can be used to make the product.

The fruits are preferably harvested between mid-June and mid-August, preferably, about mid-July. The otherwise untreated immature fruits can be used immediately or can be stored for future use. If they are stored, an ideal method is freezing. The fresh immature nuts are placed into plastic storage bags or other appropriate containers and placed in a freezer for future use.

When used fresh the nuts may be used either as single nuts and can be crushed, for example, between ones fingers, or they may be crushed in a larger press and the resulting juice bottled or otherwise stored. The juice can be used for topical use as a component in medicaments, cosmetics, soaps, shampoos, preparations and lotions for dry or other skin. In he case of the Individual user, who crushed then nut between the finger, the juice of the nut may be rubbed directly onto the skin.

The almonds can be harvested only during a small window of time to achieve the best effect. Those harvested at the optimum time can be stored in a freezer to preserve the freshness and used later by taking the frozen fruit from the freezer, thawing it, crushing it between the fingers of the user, and applying directly to the area of dry skin as reported above.

EXAMPLE

This is an example of harvesting the immature fruits, storing the immature fruits and using them to relieve symptoms of dry skin.

The fruits were harvested by hand from an almond orchard in Chico, Calif. in mid-July. The otherwise untreated immature fruits were placed into plastic storage bags and placed in a freezer for future use.

When used fresh the nuts were crushed between the fingers of the sufferer of dry skin, and the gel produced was rubbed on an area of dry skin. The sufferer reported prompt relief from the symptoms and with continued use, the symptoms abated.

The almonds can be harvested only during a small window of time to achieve the best effect. Therefore, those harvested at the right time were stored in cold storage to preserve them and used later by taking the frozen fruit from the freezer, thawing them, then crushing them between the fingers of the user and applying on the area of dry skin.

I claim:

1. A method for skin moisturization comprising:

obtaining immature almonds;

removing the fruit hull from the immature almond;

extracting the juice of the immature almond; and administering the juice of the immature almond to a portion of the skin that is in need of moisturization.

2. The method of skin moisturization of claim 1, wherein the immature almond is grown on a tree selected from the group of trees consisting of *Prusnus amygdalus, Amygdalus communis*, and *Prunus dulces*.

3. The method of skin moisturization of claim 1 wherein the extracting step comprises pressing the immature almond to extract the juice contained therein.

4. The method of skin moisturization of claim 1 further including the step of storing the juice extracted, before the administration of the juice.

5. The method of skin moisturization of claim 4 wherein the form of storing is freezing.

6. The method of ski moisturization of claim 1 wherein the administrating step includes containing the skin with the extracted juice.

7. The method of skin moisturization of claim 6 wherein the administrating step includes contacting the skin with a composition selected from the group consisting of medicinal compositions, cosmetics, soaps, and medicants.

8. A method of processing almonds to make a skin moisturizing composition comprising:

obtaining an immature almond;

removing a fruit hull from the immature almond;

pulverizing the immature almond into a juice that is applyable to the skin of a person.

9. The method of claim 8 wherein the immature almond is first crushed to produce a liquidy gel.

10. The method of claim 8 wherein the immature almond is harvested in mid-July.

11. The method of claim 8 wherein the immature almond is grown on a tree selected from the group of trees consisting of *Prusnus amygdalus, Amygdalus communis*, and *Prunus dulces*.

* * * * *